United States Patent [19]

Cordes

[11] Patent Number: 4,487,681
[45] Date of Patent: Dec. 11, 1984

[54] ELECTROPLATING TEST CELL

[75] Inventor: Franz R. Cordes, State College, Pa.

[73] Assignee: Chemcut Corporation, State College, Pa.

[21] Appl. No.: 458,668

[22] Filed: Jan. 17, 1983

[51] Int. Cl.³ .............................................. G01N 27/42
[52] U.S. Cl. ...................................... 204/434; 422/61
[58] Field of Search ............................ 204/434; 422/61

[56] References Cited

U.S. PATENT DOCUMENTS 2,149,344  3/1939  Hull ................................. 204/434 X
4,301,139  11/1981 Feingers et al. .................. 422/61 X

FOREIGN PATENT DOCUMENTS 434302  5/1974  U.S.S.R. ............................... 204/434

OTHER PUBLICATIONS

J. B. Mohler, "The Slot Cell", Metal Finishing, Jul., 1955, pp. 53–58.
J. B. Mohler, "Plating Through A Slot", Metal Industry, Sep. 11, 1953, pp. 219–222.
J. B. Mohler, "Calibration of Plating Range Cells", Metal Finishing, May, 1952, pp. 475–481.

Primary Examiner—G. L. Kaplan
Assistant Examiner—Nam X. Nguyen
Attorney, Agent, or Firm—Paul & Paul

[57] ABSTRACT

An electroplating test cell is disclosed which permits the measurement of the throwing power of an acid. The cell comprises a cathode having a member which is surrounded by an insulating tube. The tube redirects the current in the cell, thereby reducing the amount of metal deposited on the cathode. The pattern of metal deposition on the cathode can be used to estimate the throwing power of the acid in the electrolyte.

10 Claims, 5 Drawing Figures

ELECTROPLATING TEST CELL

BACKGROUND OF THE INVENTION

This invention relates to the field of printed circuit boards, and in particular, relates to the electrodeposition of metal, such as copper, on flat boards.

A typical cell for electroplating comprises a copper cathode and a copper anode, immersed in a solution of copper sulfate ($CuSO_4$). The cathode comprises the element to be plated. When the electrodes are connected to a source of direct current, the cathode is charged negatively. Some of the electrons from the cathode combine with the positively-charged copper ions ($Cu^{++}$) in the solution, to form metallic copper, which is deposited on the surface of the cathode. At the same time, the electric circuit is completed by the discharge of sulfate ions ($SO_4^{--}$) on the copper anode, forming copper sulfate which, in turn, dissolves in the solution and restores its original concentration. The reactions at the electrodes can be summarized as follows:

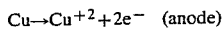

$Cu \rightarrow Cu^{+2} + 2e^-$ (anode)

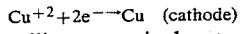

$Cu^{+2} + 2e^- \rightarrow Cu$ (cathode)

Metallic copper is thus transferred from the anode to the cathode. In the example above, the acid in the electrolyte could be sulfuric acid. Other metals and other acids may be used with many variations.

In the electroplating of circuit boards, it is necessary to measure the "throwing power" of the acid in the electrolyte. Throwing power refers to the ability of the acid to penetrate relatively remote areas of the circuit board, such as holes in the board.

There are two principal ways of measuring throwing power which have been known in the prior art. One method is by microsection, that is, the cutting of the board, and observation of the piece through a microscope. The principal disadvantage of this method is that it is very time consuming; the preparation of the board for observation is lengthy and it requires about 8 hours to obtain a measurement. Another method, known in the prior art, for measuring throwing power is the use of the Haring Blum cell, which consists of two or more small panels placed at known distances from an anode. The greater the throwing power, the greater is the amount of metal which is plated on the board further away from the anode. This technique works well for cells using tin/lead, and gold or nickel, but does not work well for acid/copper solutions which are of interest in the present application.

The present invention provides a convenient apparatus for obtaining reliable quantitative estimates of throwing power of an acid.

SUMMARY OF THE INVENTION

The present invention comprises a cell having an anode, a cathode, and an electrolyte, wherein the cathode is surrounded in part by an insulating tube which alters the current density in the cell, and reduces the amount of metal which is deposited on portions of the cathode. The variation in thickness of the metal deposited on the cathode serves as a measurement of throwing power. The more metal observed deeply into the tube, the more deeply the penetration of the acid, and the greater the throwing power.

Accordingly, it is an object of the present invention to provide a test cell for measuring, simply, reliably, and economically, the throwing power of an acid.

It is a further object of the invention to provide a test cell wherein the throwing power of the acid may be objectively measured, without reliance on judgment of a human operator.

It is a further object of the invention to provide an apparatus which can be used to predict how well an acid will penetrate all the holes in a printed circuit board.

It is a further object of the present invention to provide a cathode structure which is suitable for obtaining quantitative estimates of the throwing power of an acid.

Other objects and advantages of the present invention will be apparent to those skilled in the art, from a reading of the following brief description of the drawings, the detailed description of the invention, and the appended claims.

DETAILED DESCRIPTION OF THE INVENTION

Figure 3:
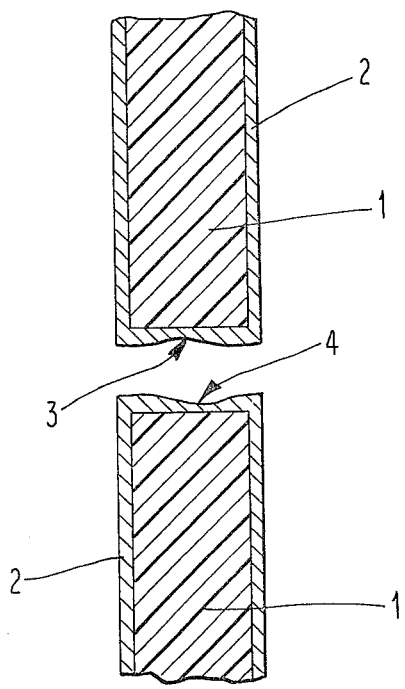
FIG. 3 is a cross-sectional view of a portion of a printed circuit board on which metal has been electrodeposited.

The present invention comprises a test cell which enables the user to measure the throwing power of an acid. Before describing the specific details of the invention, it is helpful to illustrate the concept of throwing power as it applies to the field of the invention. FIG. 3 shows a cross-sectional view of a printed circuit board which has been electroplated. FIG. 3 does not illustrate the invention, but is included only to give a graphic example of throwing power. Circuit board 1 has been immersed in a cell (not shown in FIG. 3), through which current has flowed for a period of time. Metal is deposited on the board 1 according to known chemical reactions. The layer of deposited metal is indicated by reference numeral 2. FIG. 3 shows, in cross-section, a hole in the printed circuit board, and the thickness of layer 2 at positions within the hole, as indicated by arrows 3 and 4, is less than the thickness at other locations. The positions indicated by arrows 3 and 4 are examples of locations where the throwing power of the acid is insufficient for effective electroplating of the particular board shown. An acid with greater throwing power is more likely to cause the printed circuit board to be electroplated with a more uniform thickness of metal, even in the relatively remote locations such as holes and the like.

Figure 1:
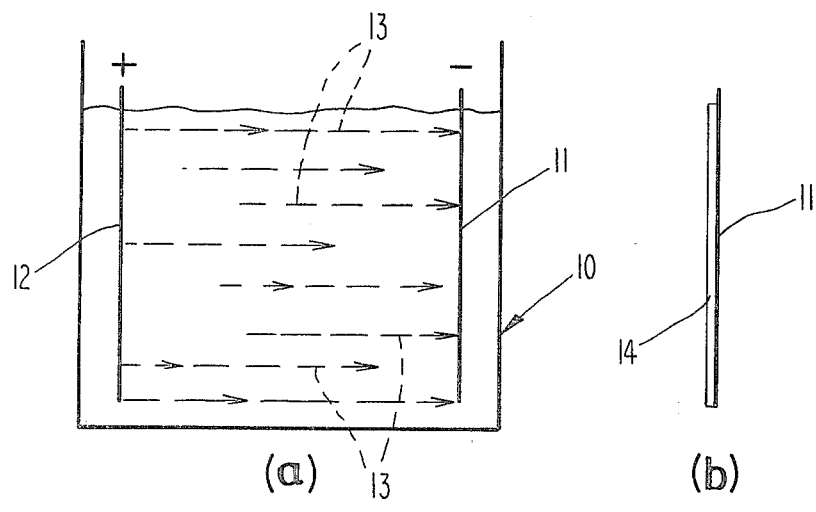
FIG. 1a is a diagram of an electroplating cell having no shielding over either of its electrodes.
FIG. 1b is a diagram illustrating the cathode of FIG. 1a after electroplating.
Figure 2:
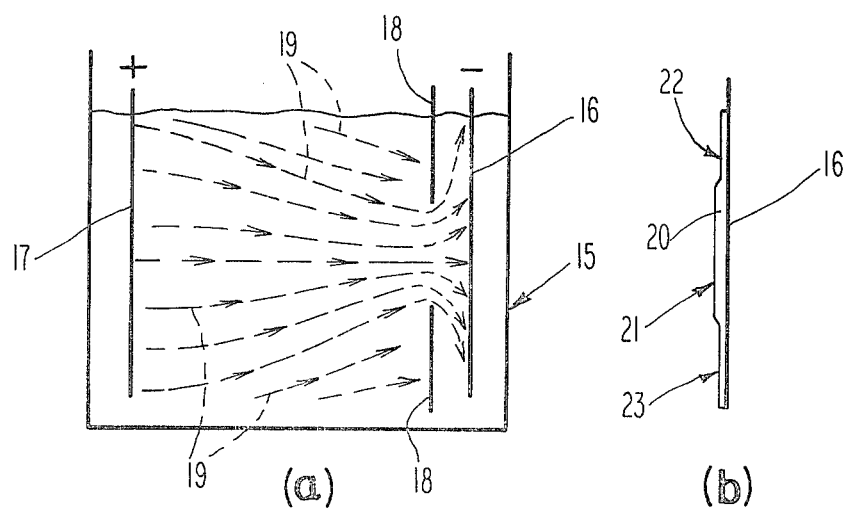
FIG. 2a is a diagram of an electroplating cell, wherein part of the cathode is shielded.
FIG. 2b is a diagram illustrating the cathode of FIG. 2a after electroplating.

The operation of the present invention is dependent on the fact that when an insulating shield is placed in front of an electrode, the current density within the cell is altered by the shield, and the thickness of deposited metal is reduced in the shielded regions. This concept is illustrated in FIGS. 1 and 2, which are also not part of the invention, but are included to illustrate the theory underlying the invention. FIG. 1a shows cell 10 having cathode 11 and anode 12. Dotted lines 13 indicate the direction of current, and the lines 13 as a whole provide a schematic picture of current density. FIG. 1b shows cathode 11 having a layer 14 of metal which has been deposited on the cathode 11 after operation of the cell 10 for a period of time. In FIG. 1b, the layer of metal 14 has substantially uniform thickness.

FIG. 2a shows, in contrast to FIG. 1a, cell 15 having cathode 16 and anode 17, but further comprising an insulating shield 18 which shields part of cathode 16. The altered current pattern is indicated by lines 19. Clearly, shield 18 has altered the current density in the cell. FIG. 2b shows cathode 16 after electrodeposition, with layer 20 of metal deposited thereon. The layer of metal 20 is the thickest at the location indicated by arrow 21, and thinner at the locations indicated by arrows 22 and 23. The latter locations correspond to the locations which were partially obscured by shield 18.

Figure 4:
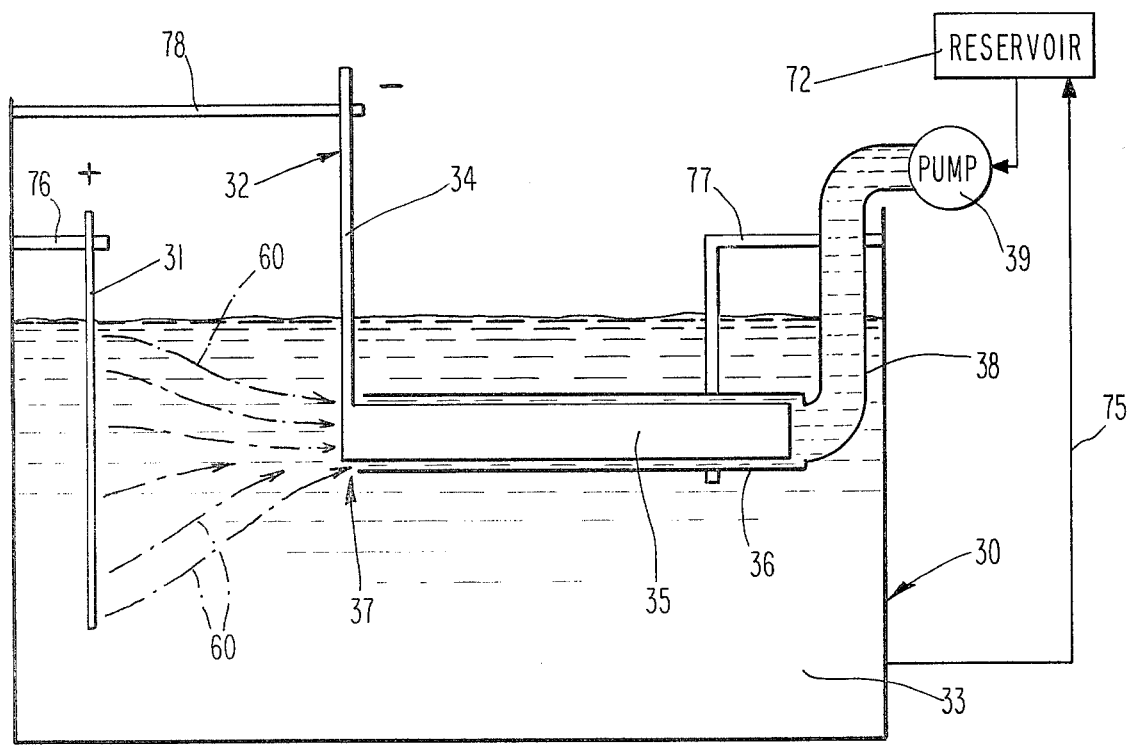
FIG. 4 is a partially schematic, elevational view of the electroplating test cell of the present invention.

The electroplating test cell of the present invention is illustrated, partially schematically, in FIG. 4. Cell 30 has an anode 31 and a cathode indicated generally by reference numeral 32. The anode and cathode are immersed in electrolyte 33. Cathode 32 comprises members 34 and 35. Cathode 32 is preferably of unitary construction, and is in the form of a flat metal strip. Members 34 and 35 are thus parts of the same piece of metal. Member 35 of cathode 32 extends longitudinally as shown in FIG. 4 and is surrounded by an insulating tube 36, which is preferably cylindrical, and which is constructed of glass or a plastic, such as polyvinylchloride (PVC). Tube 36 is open at one end, which end is indicated by arrow 37. The other end of tube 36 is connected to conduit 38 which is connected, in turn, to pumping means 39 which pumps the electrolyte solution through the tube to provide turbulence. The pumping means 39 pumps electrolyte solution from reservoir 72. Return conduit 75 allows electrolyte to flow from the cell back to the reservoir.

Also shown in FIG. 4 are holding means 77, for holding tube 36 and conduit 38 in place, as well as insulating holding means 76 and 78, for holding the anode 31 and cathode 34, respectively, for electrical connection thereto to portions thereof that protrude out of the electrolyte, at (+,−) respectively.

Figure 5:
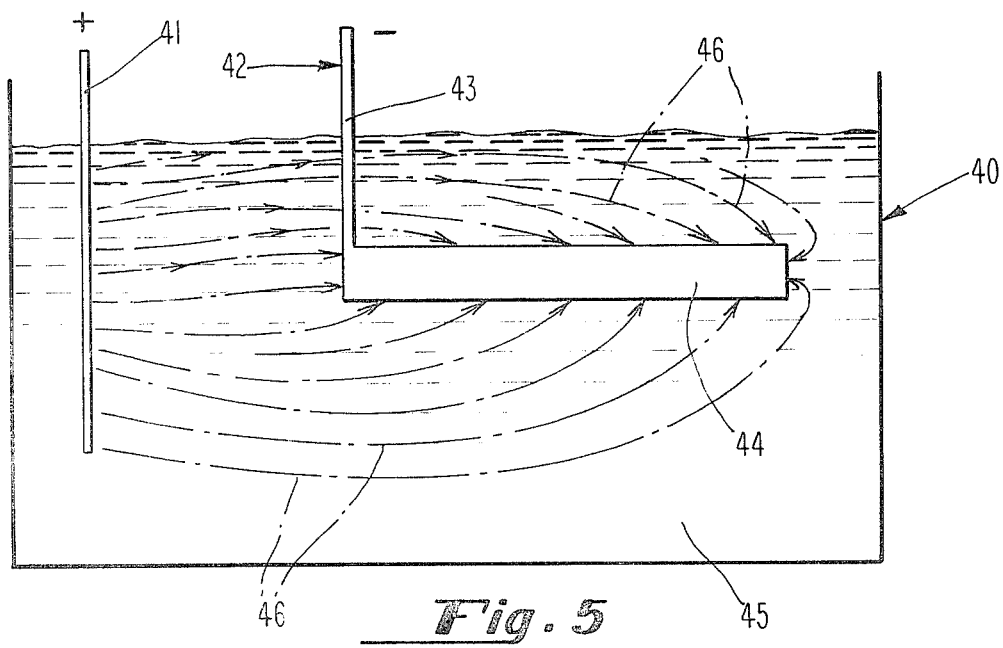
FIG. 5 is a partially schematic, elevational view of an electroplating cell which does not have an insulating tube surrounding a portion of the cathode.

The invention, as illustrated in FIG. 4, can best be understood in its operation by comparing it to the cell shown in FIG. 5. The cell in FIG. 5 resembles that of FIG. 4 except that the cell in FIG. 5 has no insulating tube surrounding the cathode. For purposes for clarity, no holding means are shown in FIG. 5. The cell, indicated by referance numeral 40, has an anode 41, a cathode 42 having members 43 and 44, both electrodes being immersed in electrolyte 45. However, in the cell of FIG. 5, when the current is turned on, the current density appears as shown by lines 46. As shown in FIG. 5, all of member 44 of cathode 42 will be subjected to the current, and the layer of metal plated along the cathode will be of substantially uniform thickness.

In the present invention, as illustrated in FIG. 4, the current density is dramatically altered by the presence of tube 36, the current density being indicated by lines 60. Because of the shielding effect of tube 36, as discussed with reference to FIGS. 1 and 2, the current is forced into a different configuration, and the plating on member 35 of cathode 32 is not uniform. The thickness of deposited metal is greatest at the end of the member 35 indicated by arrow 37. The thickness of the deposited metal decreases as one progresses into the interior of tube 36. If member 35 is sufficiently long, there will be a point at which there will be no deposited metal at all. Therefore, the thickness of the deposited metal along member 35 is made to vary from a high level, near the opening of the tube 36, to a point at which the metal is no longer present, that point being more deeply into the interior of tube 36. The thickness of the metal deposite at each point along member 35 is an indication of the throwing power of the acid in electrolyte 33.

In the operation of the electroplating test cell of the present invention, the solution is agitated through tube 36, by pump 39 and electroplating is accomplished for about one half hour. The purpose of the agitation is to maintain uniformity of concentration of the electrolyte. In practice, the amount of solution pumped per unit of time would be fixed at a certain level, as would other cell parameters such as size of electrodes. Standardization of parameters would enhance the utility of the invention as a testing device.

One would then obtain measurements of the thickness of the metal deposits (which would be of the order of 1 mil), at the entrance of tube 36 (near arrow 37) and then at intervals of one half inch. In one embodiment, the glass tube might have a diameter of about 5 millimeters, with a length of 100 millimeters. That is, the tube has an aspect ratio of about 20, the aspect ratio being defined as the ratio of tube thickness to tube diameter. In most printed circuit boards, aspect ratios of 8 are common. Thus, the tube shown in the present invention, with an aspect ratio of 20, allows for measurement of acids having a wide range of throwing powers.

Measurement of the thickness of the metal deposits on member 35 of cathode 32 is best accomplished by using a betascope, which directs electrons towards the surface of the deposits, and derives an indication of thickness of the deposit by measuring the degree to which the electrons are reflected. By using a betascope, the process is accomplished in only a few minutes. Betascopes are commercially available, and are well known to those skilled in the art.

After having obtained measurements of the thickness of the metal deposits at various intervals along the cathode it is possible to derive a useful index of throwing power. Many indices could be used. For example, one could compute the average thickness at the first three points, and then compute the average thickness of the last three points, and then compute the ratio of the two averages. Many other indices can be computed from the data which would give the same information. What is important is that the index reflect the difference in metal thickness at points along the cathode, thereby giving a measureable indiction of the throwing power of the acid.

It is clear that the objects of the invention are fulfilled by the above disclosure. The specific details of the invention can be varied within the scope of the invention. For example, the composition of the tube, the length and diameter of the tube, and the precise chemical constituents of the electrodes and electrolyte may be varied, all within the spirit and scope of this invention. It is accordingly noted that the following claims are not to be deemed limited to this one embodiment, but are to be interpreted to cover these and other modifications which would be apparent to those skilled in the art.

What is claimed is:

1. An electroplating cell for measuring the throwing power of an acid, comprising:
   a container for receiving an electrolyte therein,
   an anode in the container with at least a protion of the anode adapted to be disposed in the electrolyte, and another portion of the anode being suitably disposed for electrical connection thereto,
   a cathode in the container, with at least a longitudianlly disposed portion of the cathode adapted to be disposed in the electrolyte, and with another portion of the cathode being suitably disposed for electrical connection thereto, and
   a longitudinally disposed insulating tube means surrounding at least a major portion of the cathode along substantially its entire length and comprising means facilitating substantially longitudinal flow of current in the electrolyte along the surrounded portion of the cathode, when electrical connection ia made to suitable portions thereof, wherein the tube means is a tube that is open at one end, so as to permit the electrolyte to enter the region between the cathode and the tube, wherein the tube is connected to a pumping means, the pumping means being connected to pump the electrolyte through the tube.

2. The electroplating cell of claim 1, wherein the tube is constructed of glass.

3. The electroplating cell of claim 1 wherein the tube is constructed of plastic.

4. The electroplating cell of claim 1, wherein the tube is generally cylindrically shaped, and wherein the tube is concentric with at least part of the cathode.

5. The electroplating cell of claim 1, wherein the pumping means comprises means for agitating the electrolyte through the tube, the agitating means being connected to the end of the tube which is opposite to the open end of the tube.

6. An electroplating cell for measuring the throwing power of an acid, comprising:
   a container for receiving an electrolyte therein,
   an anode in the container with at least a portion of the anode adapted to be disposed in the electrolyte, and another portion of the anode being suitably disposed for electrical connection thereto,
   a cathode in the container, with at least a longitudinally disposed portion of the cathode adapted to be disposed in the electrolyte, and with another portion of the cathode being suitably disposed for electrical connection thereto, and
   a longitudinally disposed insulating tube means surrounding at least a major portion of the cathode along substantially its entire length and comprising means facilitating substantially longitudinal flow of current in the electrolyte along the surrounded portion of the cathode, when electrical connection is made to suitable portions thereof, wherein the tube means is a tube that is open at one end, so as to permit the electrolyte to enter the region between the cathode and the tube, wherein the tube is connected to a pumping means, the pumping means being connected to pump the electrolyte through the tube, wherein the tube is generally cylindrically shaped, and wherein the tube is concentric with at least part of the cathode, wherein the pumping means comprises means for agitating the electrolyte through the tube, the agitating means being connected to the end of the tube which is opposite to the open end of the tube, and wherein the tube, the cathode, and the anode are held in place by support means carried by the container.

7. A kit for constructing an electroplating test cell for measuring the throwing power of an acid, the kit comprising box means for containing electrodes and electrolyte, the box means comprising means facilitating the attachment of electrodes to be carried by the box means, a first electrode, a second electrode, and a glass tube, shaped to comprise means surrounding a longitudinally disposed portion of the second electrode, and comprising means facilitating substantially longitudinal flow of current in the electrolyte along the surrounded portion of the second electrode, when the electroplating test cell is operating, further comprising pumping means adapted to be connected to the tube.

8. The kit of claim 7, further comprising conduit means adapted to be connected to the pumping means and to the tube.

9. The kit of claim 8, further comprising return conduit means, adapted to be connected to the box and to the pumping means.

10. The kit of claim 9, wherein the second electrode comprises a unitary strip of metal, the strip having two elongated members, and wherein the tube is constructed to fit substantially over the entire length of one of the members of the cathode.

* * * * *